United States Patent [19]

Seiter et al.

[11] Patent Number: 4,643,878
[45] Date of Patent: Feb. 17, 1987

[54] EXTRACTION CELL

[75] Inventors: George M. Seiter, Minneapolis; Loren J. Klitzke, Long Lake; Iver L. Nelson, Minneapolis, all of Minn.

[73] Assignee: Waldorf Corporation, St. Paul, Minn.

[21] Appl. No.: 662,639

[22] Filed: Oct. 18, 1984

[51] Int. Cl.$^4$ .................. B01L 11/00; G01N 30/00
[52] U.S. Cl. .................... 422/101; 422/102; 422/266; 220/94 R; 220/327; 248/145.3; 248/145.6; 248/151; 248/188.8; 436/178
[58] Field of Search ............... 422/101, 102, 242, 237, 422/236, 266; 436/178; 220/94 R, 327; 248/151, 145.3, 145.6, 188.1, 188.8, 176

[56] References Cited

U.S. PATENT DOCUMENTS

| | | | |
|---|---|---|---|
| 57,135 | 8/1866 | Hoffstadt | 422/242 |
| 1,012,302 | 12/1911 | Van Horn | 248/151 |
| 1,803,306 | 4/1931 | Stengel | 422/242 |
| 2,633,414 | 3/1953 | Boivinet | 422/242 |
| 2,881,776 | 4/1959 | Wrage | 220/94 R |
| 3,270,906 | 9/1966 | Christensen | 422/242 |
| 3,947,251 | 3/1976 | Quame | 422/102 |
| 4,233,697 | 11/1980 | Cornwall | 220/327 |
| 4,253,583 | 3/1981 | Lynch | 220/327 |
| 4,317,726 | 3/1982 | Shepel | 422/101 |
| 4,494,666 | 1/1985 | Cooper | 220/327 |

Primary Examiner—Wilbur Bascomb
Attorney, Agent, or Firm—Dorsey & Whitney

[57] ABSTRACT

A toxic substance extraction cell includes a chamber for housing a heated solvent, a pair of gaskets adapted to be seated on the solvent housing between which is clamped a specimen to be tested; the space between the gaskets being liquid tight, and a cover for clamping the gaskets to the solvent housing. After assembly of the cell with the preheated solvent in the housing and the specimen to be tested between the gaskets, the cell is inverted and supported on a plurality of legs provided on the cover. The solvent is thus placed in contact with the specimen in order to dissolve any toxic substances contained within the specimen. The cell is then reinverted and supported on a suitable stand and allowed to cool, disassembled, and the solvent removed and tested for toxic residue.

7 Claims, 4 Drawing Figures

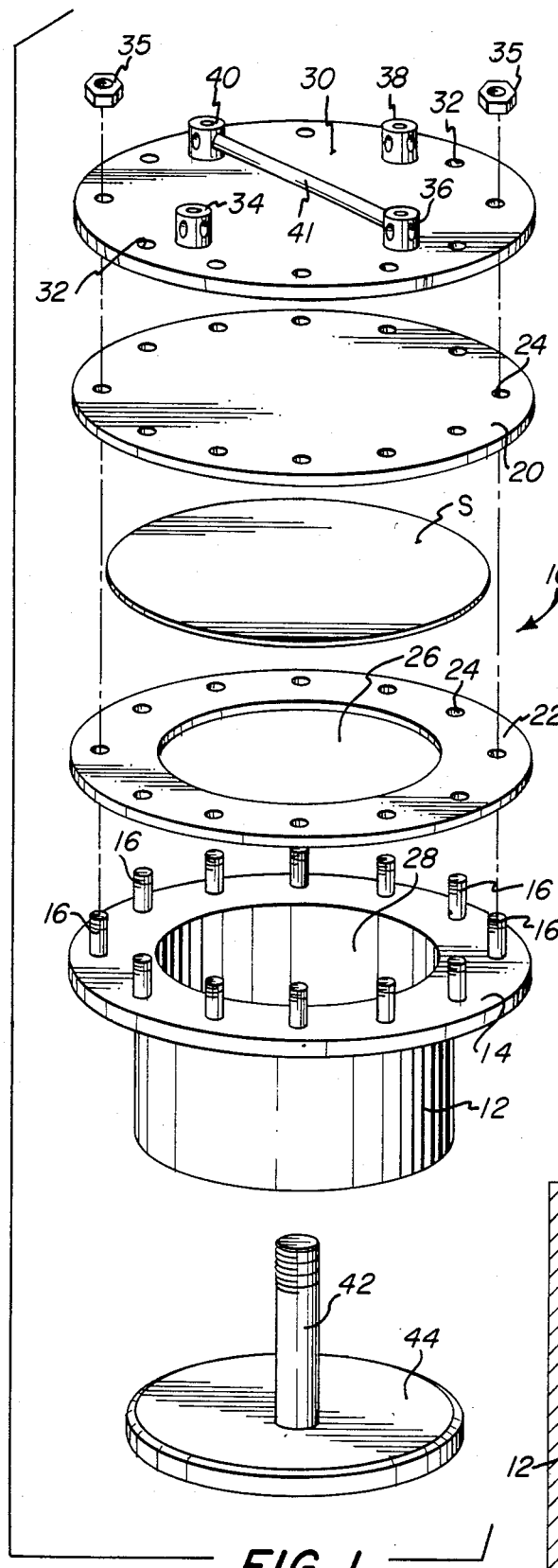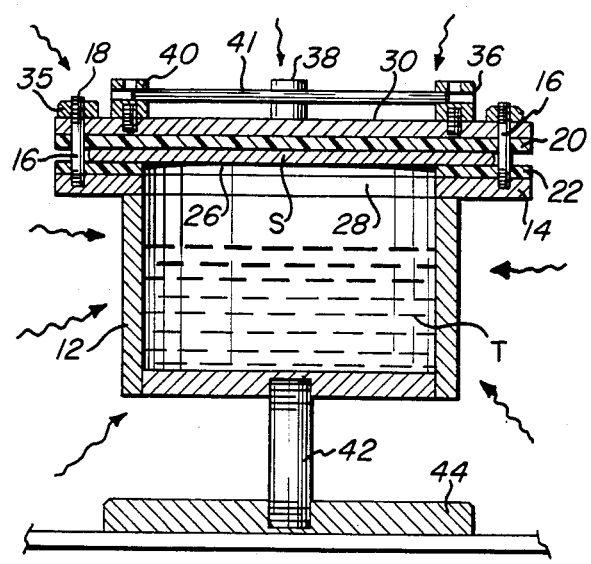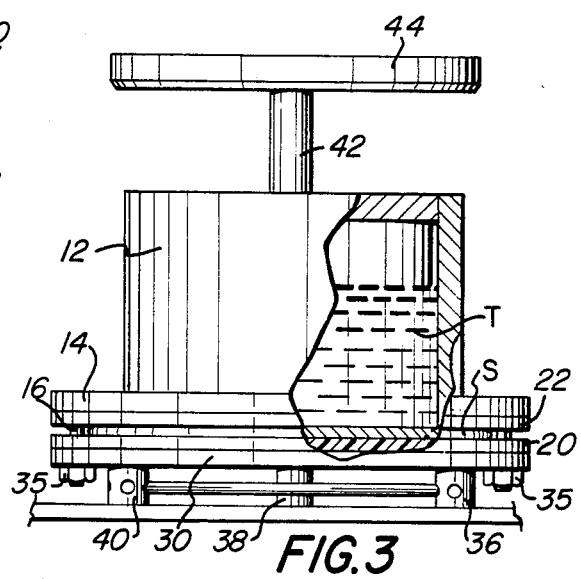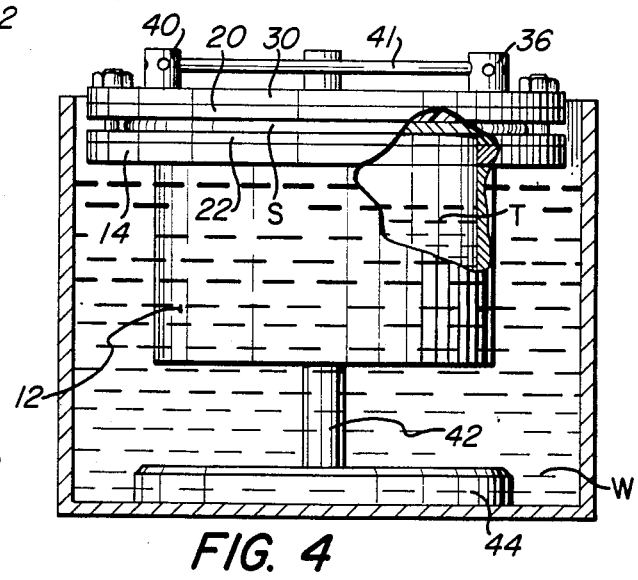

EXTRACTION CELL

BACKGROUND AND SUMMARY OF THE INVENTION

This invention relates to testing apparatus, and more particularly, a device for extracting toxic substances from a specimen, such as paperboard, so as to accurately determine the level of the toxicity present in the specimen.

With the advent of Federal regulations requiring that the level of potentially toxic substances in cardboard or paperboard food containers be held below certain minimum levels, it has become necessary to test such materials in order to be able to determine whether any potentially toxic substances exist in the paperboard or cardboard and if so, to what degree they do exist, as they must be held below certain predescribed limits. In order to accomplish this purpose, it was necessary to develop apparatus for testing for toxic substances which may be present in cardboard or paperboard samples formed into food containers. This invention relates to such an apparatus.

In accordance with the present invention, a toxic substance extraction cell is provided consisting of a chamber for housing a heated solvent, a pair of gaskets adapted to be seated on the solvent housing between which is clamped the specimen to be tested; the space between the gaskets being liquid tight, and a cover for clamping the gaskets to the solvent housing. After assembly of the cell with the preheated solvent in the housing and the specimen to be tested between the gaskets, the cell is inverted and supported on a plurality of legs provided on the cover. The solvent is thus placed in contact with the specimen in order to dissolve any toxic substances contained within the specimen.

The cell is then reinverted and supported on a suitable stand and allowed to cool, by placing the cell for example, in a water bath. The cell is then disassembled and the solvent removed and tested for toxic residue.

BRIEF DESCRIPTION OF THE DRAWING

Further objects and advantages of the invention will become more apparent from the following description and claims, and from the accompanying drawing, wherein:

FIG. 1 is an exploded perspective view of the extraction cell of the present invention;

FIG. 2 is a longitudinal cross-sectional view of the assembled components of the extraction cell of FIG. 1 and further illustrating the initial step involved in using the cell;

FIG. 3 is a front view in elevation of the cell of FIG. 1 with portions broken away and illustrated in section, which cell has been inverted to enable the solvent to contact the specimen being tested and clamped within the cell; and FIG. 4 is a view similar to FIG. 3, but with the cell reinverted and being cooled in a water bath.

DETAILED DESCRIPTION OF THE PREFERRED EMBODIMENT

Referring now to the drawing in detail, wherein like numerals indicate like elements throughout the several views, the components of the extraction cell of the present invention is illustrated in general in FIG. 1 by the numeral 10.

The extraction cell 10 includes a cylindrical solvent housing 12 having a larger diameter circular flange 14 provided along its outer circumference with a plurality of upright pins 16 threadedly engaged in the flange 14. The opposite end of each of the pins 16 is also threaded as indicated at 18.

A pair of Teflon gaskets 20 and 22 which are also circular in configuration are provided. Each of the gaskets includes a plurality of holes 24 about its outer circumference adapted to receive one of the pins 16 therethrough. The gasket 22 includes a circular opening 26 corresponding to the dimensions of the opening 28 in the solvent housing 12 and when the gaskets are placed over the pins 16, the openings 26 and 28 are placed in corresponding registration.

A cover element 30 of the same dimensions as the flange 14 is provided. The cover element 30 also includes a plurality of openings 32 about its outer circumference, each of which is also adapted to receive one of the pins 16 therethrough. A plurality of nuts 35 are adapted to be received on the outer threaded ends 18 of each of the rods 16 to clamp the cover and gaskets to the solvent housing 12 and form a liquid seal along the outer periphery of the clamped elements.

Four upstanding studs 34, 36, 38 and 40 are provided on the exposed surface of cover element 30. The studs 36 and 40 are connected by a radially extending bar 41 so that the bar 41 and studs 36, 40 can provide a handle for grasping and removing the cover from the extraction cell. The studs 34, 36, 38 and 40 also perform the function of providing support legs for the cell when it is inverted as described below.

In use, a suitable circular specimen S from a piece of cardboard or paperboard to be tested is removed and placed between the gaskets 20 and 22 over the opening 26. A suitable preheated solvent T is placed within the housing 12 through the opening 28. The gaskets 20 and 22 are then placed in registration with the rods 16 and the cover applied over the gaskets and the nuts 42 tightened so that the cover 30, gaskets 20, 22, specimen S, and solvent housing 12 are clamped together as a unit and threadedly connected to a standard 42 on a support base 44. The cell 10 is then placed in an upright condition in an oven and reheated, as illustrated in FIG. 2.

After a predetermined temperature has been reached, the cell is then inverted and supported upon the stud legs 34, 36, 38 and 40 provided on the exterior surface of the cover 30, as shown in FIG. 3. The solvent T within the housing 12 will come in contact with the specimen S overlying the registered openings 26 and 28 to dissolve any toxic substances being tested for which may be present in the specimen.

The cell 10 is then reinverted as shown in FIG. 4 and the solvent is allowed to cool by placing the cell in a water bath W. Then the cell 10 is opened by removing the nuts 35 and disassembling the components of the cell, and the solvent evaporated and tested for toxic residue.

What is claimed is:

1. An extraction cell for testing the toxicity in a specimen housed within the cell by enabling it to contact a suitable solvent adapted to dissolve any toxic substances in the specimen, comprising:
    a housing adapted to receive a quantity of said solvent,
    said housing including
    a centrally located opening and a rigidly-affixed flange;

a plurality of pins having at least one threaded end extending upwardly from the flange of said solvent housing;

at least one gasket member having a centrally located specimen exposure opening adapted to be placed in registration with the centrally located opening in said solvent housing and including a plurality of pin openings extending about the circumference thereof adapted to receive the pins extending upwardly from said solvent housing flange therethrough; and a cover element adapted to clamp a specimen placed over the specimen exposure opening in said gasket to said solvent housing in liquid-tight sealed engagement against the flange of the housing, said cover including a plurality of pin openings extending about its circumference adapted to receive the upright pins on said solvent housing therethrough, means received on the threaded end of said pins for clamping said cover, gasket and a specimen to be tested to said solvent housing in liquid-tight sealed engagement, and support means on said cover element for supporting said extraction cell in an inverted position in which the solvent contacts the specimen.

2. The extraction cell of claim 1 wherein said support means on said cover includes a plurality of studs extending upwardly from the outer surface of said cover element.

3. The extraction cell of claim 1 including
a second gasket between said cover and said first gasket for aiding in providing a liquid-tight seal adjacent the outer periphery of said extraction cell, said second gasket including a plurality of openings adjacent its periphery receiving said pins therethrough.

4. The extraction cell of claim 1 including
a stand connected to said solvent housing for supporting said extraction cell in an upright position.

5. The extraction cell of claim 3 including
a stand connected to said solvent housing for supporting said extraction cell in an upright position.

6. The extraction cell of claim 2 including
a bar extending between a pair of said studs to provide a hold for raising said cover.

7. The extraction cell of claim 1 wherein the specimen is a substantially planar piece of sheet material and the centrally located opening in the housing and centrally located specimen exposure opening are slightly smaller in area than the specimen.

* * * * *